US010144702B2

(12) United States Patent
Verkuijl et al.

(10) Patent No.: US 10,144,702 B2
(45) Date of Patent: Dec. 4, 2018

(54) METHOD FOR THE MANUFACTURE OF N,N-DIALKYLLACTAMIDE

(71) Applicant: PURAC BIOCHEM BV, Gorinchem (NL)

(72) Inventors: Bastiaan Jeroen Victor Verkuijl, Gorinchem (NL); Jurgen Cornelis Henricus Maas, Gorinchem (NL)

(73) Assignee: PURAC BIOCHEM B.V., Gorinchem (NL)

( * ) Notice: Subject to any disclaimer, the term of this patent is extended or adjusted under 35 U.S.C. 154(b) by 0 days.

(21) Appl. No.: 15/516,352

(22) PCT Filed: Oct. 1, 2015

(86) PCT No.: PCT/EP2015/072651
§ 371 (c)(1),
(2) Date: Mar. 31, 2017

(87) PCT Pub. No.: WO2016/050894
PCT Pub. Date: Apr. 7, 2016

(65) Prior Publication Data
US 2017/0298009 A1  Oct. 19, 2017

(30) Foreign Application Priority Data
Oct. 3, 2014 (EP) .................................... 14187613

(51) Int. Cl.
C07C 231/02 (2006.01)
C07C 231/16 (2006.01)
C07C 231/24 (2006.01)
C07C 235/06 (2006.01)

(52) U.S. Cl.
CPC .......... *C07C 235/06* (2013.01); *C07C 231/02* (2013.01); *C07C 231/16* (2013.01); *C07C 231/24* (2013.01)

(58) Field of Classification Search
CPC ... C07C 235/06; C07C 231/02; C07C 231/16; C07C 231/24
See application file for complete search history.

(56) References Cited

U.S. PATENT DOCUMENTS

| | | | | |
|---|---|---|---|---|
| 2,539,473 | A | | 1/1951 | Ratchford et al. |
| 3,480,671 | A | * | 11/1969 | Baker .................... A01N 39/02 504/338 |
| 4,358,612 | A | * | 11/1982 | Gless, Jr. ............. C07C 231/02 554/67 |
| 7,297,802 | B2 | * | 11/2007 | Wang .................... C07C 45/673 549/419 |
| 8,309,765 | B2 | * | 11/2012 | Shroff .................. C07C 231/12 504/338 |
| 8,440,860 | B2 | | 5/2013 | Van Krieken |
| 2013/0079547 | A1 | * | 3/2013 | Yoon ........................ C07C 67/40 560/179 |

FOREIGN PATENT DOCUMENTS

| | | | |
|---|---|---|---|
| CN | 103232344 | * | 7/2013 |
| EP | 0072884 | A2 | 3/1983 |
| GB | 2482299 | * | 2/2012 |
| JP | S58-035154 | A | 3/1983 |
| JP | 2009-518380 | A | 5/2009 |
| JP | 2010-526059 | A | 7/2010 |
| JP | 2012-516307 | A | 7/2012 |
| WO | 2007/066164 | A1 | 6/2007 |
| WO | 2007/107745 | A2 | 9/2007 |
| WO | 2009/004642 | A2 | 1/2009 |
| WO | 2010/037776 | A1 | 4/2010 |
| WO | 2010/086394 | A1 | 8/2010 |

OTHER PUBLICATIONS

Christensen et al., "Synthesis and Properties of Substituted 1,6-Dioxapyrene Donors," J. Org. Chem. 1991, 56, 7055-7058 (Year: 1991).*
English Translation of CN103232344, Jul. 8, 2013, pp. 1-7 (Year: 2013).*
Ratchford et al., "Preparation of N,N-Dimethylacrylamide by Pyrolysis of N,N-Dimethyl-α-Acetoxypropionamide," J. Am. Chem. Soc., 1947, 69 (8), pp. 1911-1914 (Year: 1947).*
Fleer et al., "Optimization of the use of a chiral bio-based building block for the manufacture of DHPPA, a key intermediate for propionate herbicides," Green Chemistry, 2014, vol. 16, pp. 3993-3998.
Charville et al., "The thermal and boron-catalysed direct amide formation reactions: mechanistically understudied yet important processes," Chem. Comm., 2010, vol. 46, pp. 1813-1823.
Dec. 11, 2015 International Search Report issued in International Patent Application No. PCT/EP2015/072651.
Dec. 11, 2015 Written Opinion of the International Searching Authority issued in International Patent Application No. PCT/EP2015/072651.
Jan. 4, 2018 Office Action dated Chinese Patent Application No. 201580053358.3.
W. P. Ratchford et al., "Preparation of N,N-Dimethylacrylamide by Pyrolysis of N,N-Dimethyl-α-Acetoxypropionamide," Journal of the American Chemical Society, vol. 69, pp. 1911-1914, 1947.

(Continued)

*Primary Examiner* — Pancham Bakshi
*Assistant Examiner* — Mark R Luderer
(74) *Attorney, Agent, or Firm* — Oliff PLC

(57) ABSTRACT

A method for the manufacture of N,N-dialkyllactamide, whereby at least one of the compounds selected from the series made of alkyl lactate, lactide and polylactic acid is mixed with dialkylamine in order to form a reaction mixture, under conditions whereby aminolysis takes place in the reaction mixture. The method is characterized in that the reaction mixture further includes a Lewis acid. As a result of the method, N,N-dialkyllactamides can be manufactured in high yields and with high optical purity.

17 Claims, No Drawings

(56) References Cited

OTHER PUBLICATIONS

Gless, Jr. et al., "Lewis acid mediated aminolysis of esters. Conversion of methyl (S)-(−)-2-chloropropionate to (S)-(+)-N,N-diethyl-2-chloropropionamide," Synthetic Communications, vol. 16(6), pp. 633-638, 1986.
Sakurai et al., "Preparation of derivatives of nitrogen mustard having structure of α-amino acid amide," Chemical & Pharmaceutical Bulletin, vol. 13(5), pp. 594-598, 1965.
Mar. 29, 2018 Office Action issued in Japanese Patent Application No. 2017-516873.

* cited by examiner

METHOD FOR THE MANUFACTURE OF N,N-DIALKYLLACTAMIDE

FIELD OF THE INVENTION

The invention relates to a method for the manufacture of N,N-dialkyllactamide, whereby at least one of the compounds selected from the series consisting of alkyl lactate, lactide and polylactic acid is mixed with dialkylamine in order to form a reaction mixture, under conditions whereby aminolysis takes place in the reaction mixture. The compound N,N-dialkyllactamide, especially the optically pure (R)-enantiomer of it, appears to be an interesting precursor compound in the manufacture of certain herbicides, like Napropamide-M®.

BACKGROUND OF THE INVENTION

A method of the type described in the opening paragraph is known as such, for example from the U.S. Pat. No. 8,440,860 B2, granted in the name of the present applicant. More particularly, this document discloses a method in which solid lactide is mixed with anhydrous dimethylamine at room temperature. The examples show that substantial conversion of the lactide into N,N-dimethyllactamide could only be achieved at high temperature and prolonged reaction times. Thus, a concentration of about 85% N,N-dimethyllactamide was obtained in the reaction mixture after a reaction time of 4 hours at 103° C. Under these conditions, degradation of the reaction product may be expected. In view of this, the overall efficiency of this process is relatively low. Moreover, the optical purity of the desired reaction product may decrease due to occurrence of racemization within the lactate-part of the produced N,N-dimethyllactamide. Preliminary experiments have shown that such racemization is even more pronounced in the production of N,N-diethyllactamide under the conditions disclosed in the cited patent document.

A similar method is known from the USA patent document with grant number U.S. Pat. No. 2,539,473. This patent document describes a method of producing N,N-diethyllactamide whereby lactic acid oligomer compound having a degree of polymerization of about 11 is refluxed with diethylamine at high temperatures for more than 40 hours in order to obtain a substantial amount of N,N-diethyllactamide. Again, these conditions promote the formation of degradation products originating from the desired N,N-diethyllactamide as well as extensive racemization.

OBJECT OF THE INVENTION

It is an object of the present invention to manufacture the desired N,N-dialkyllactamides in high yield at relatively low temperature (i.e. below 50° C., and preferably at room temperature) and preferably with a high conversion rate of the aminolysis, which should preferably be completed within 4 hours. More particularly, with the method according to the invention it should be feasible to obtain optically pure N,N-dialkyllactamides. So, no or almost no racemization should occur under the applied reaction conditions. Another objective is the provision of an efficient process to produce Napropamide with optically pure (R)—N,N-diethyllactamide as obtainable with the present invented method.

SUMMARY OF THE INVENTION

At least one of these objects or possible other objects is achieved by means of the method for the manufacture of N,N-dialkyllactamide, whereby at least one of the compounds selected from the series consisting of alkyl lactate, lactide and polylactic acid is mixed with dialkylamine in order to form a reaction mixture, under conditions whereby aminolysis takes place in the reaction mixture, said method being characterized according to the invention in that the reaction mixture further comprises a Lewis acid.

Lewis acids are known as compounds which can act as an electron-pair acceptor under appropriate conditions, and which are therefore able to react with a Lewis base to form a Lewis adduct by sharing the electron pair furnished by the Lewis base. Typical Lewis acids which can be used with advantage in the method according to the present invention are water-free Ferric Chloride ($FeCl_3$), and Aluminum Bromide ($AlBr_3$).

The inventors have found that adding a Lewis acid to the reaction mixture of dialkylamine with at least one of alkyl lactate, lactide and polylactic acid results in an unexpected quick aminolysis under formation of N,N-dialkyllactamide. As a result, the aminolysis can take place at low temperature, and even at room temperature. The invented method is believed to work well for different types of alkyl lactates, such as methyl lactate, ethyl lactate and propyl lactate.

Lactide can also be used with great advantage as starting compound for the aminolysis reaction according to the present invention. As regards lactide, the reaction has shown to work well with any of the isomers L,L-lactide, D,D-lactide and D,L-lactide (or meso-lactide). A 50/50 mixture of L,L-lactide and D,D-lactide (also called rac-lactide) can be used as well in the inventive method.

The invented process can also be executed while using polylactic acid (PLA) with low (5<n<20), medium (20<n<50) or high (n>50) polymerization grade as starting compound for the aminolysis (n stands for number of lactate units in the PLA polymer). Experiments, in which the conversion rates of the three groups of starting compounds were compared under identical reaction conditions, showed that the conversion rate of lactide is highest. The inventive concept appeared however not to work with lactic acid as a starting compound.

Is has further been shown that the method according to the present invention appears to work well for different types of dialkylamines, such as dimethylamine and methylethylamine. However, the increase of the conversion rate under the influence of the Lewis acid is especially observed in the aminolysis in which diethylamine was used together with at least one of the starting compounds.

An interesting embodiment of the method according to the present invention is characterized in that aluminum chloride ($AlCl_3$) is used as a Lewis acid. Compared to other Lewis acids, the use of aluminum chloride is preferred in the claimed method since $AlCl_3$ appears to result in a very high conversion rate and is easy to handle under mass production circumstances. Moreover, no racemization could be detected when using $AlCl_3$ as a Lewis acid in the method according to the invention. It is known that in the absence of Lewis acids like $AlCl_3$ such undesired racemization can easily occur during aminolysis, especially when this reaction is performed at relatively high temperatures, i.e. higher than 50° C., and/or prolonged conversion times, i.e. of for example 4 hours or more.

Also interesting is the variant of the invented method which has the characteristic that the at least one compound is optically pure. With the expression 'optically pure' it is meant that at least 99.0%, preferably more than 99.5% and most preferably more than 99.9% of the lactate-units in the produced N,N-dialkylactamide have either the enantiomeric (S)-configuration or its mirror-image, the enantiomeric (R)-configuration. It has appeared that the optical purity of the starting product is maintained in the described aminolysis reaction when using a Lewis acid, especially AlCl$_3$. Thus, no measurable racemization takes place during the aminolysis of optically pure alkyl lactate, optically pure lactide and optically pure polylactic acid under the conditions used in the execution of the method according to the present invention. This makes this method especially suitable for the production of optically pure N,N-dialkyllactamides in general, of which optically pure (R)—N,N-dimethyllactamide is an interesting example.

The optical purity (i.e, the relative amounts of the desired and not-desired lactate enantiomers) of the N,N-dialkyllactamide manufactured according to the method of the invention can be determined by means of Gas Chromatography, using a β-cyclodextrine column for separating both enantiomers. The stereochemical purity of the starting materials alkyl lactate, lactide and polylactic acid can be measured with the same method, after having these compounds converted into methyl lactate. Latter conversion is feasible without any racemization of the lactate moieties in the starting materials.

Another interesting embodiment of the present invention is characterized in that the amount of the Lewis acid in the reaction mixture is in the range of 0.3-1.2 mole equivalents, based on the amount of lactic acid units of the starting compounds added to the reaction mixture. If the added mole equivalent of the Lewis acid is less than 0.3, the risk that no complete aminolysis occurs will increase. Addition of more than 1.2 mole equivalents of Lewis acid does not add anymore to a complete aminolysis, and is therefore not preferred in view of cost considerations. To avoid both mentioned disadvantages, it is preferred to have an amount of the Lewis acid in the reaction mixture in the range of 0.5-1.0 mole equivalents, based on the amount of lactic acid units of the compounds in the reaction mixture.

A further interesting embodiment of the present invention is characterized in that alkyl stands for at least one of methyl or ethyl, preferably for ethyl. Thus the amine used is preferably dimethylamine, methylethylamine and preferably diethylamine. With these amines, the relatively simple compounds N,N-dimethyllactamide, N,N-methylethyllactamide and N,N-diethyllactamide can be manufactured with the invented method with high yields and with high optical purity, whereby the latter diethyl compound is commercially the most attractive compounds of the three mentioned, especially in its optically pure enantiomeric (R)-form. It has been found that latter optically pure compound can be used in an efficient method to produce the optically pure compound (R)—N,N-diethyl-2-(1-naphthalenyloxy)propanamide. This compound is known under the commercial name Napropamide-M®.

Much interest is also given to the embodiment of the present invention, which is characterized in that the reaction mixture comprises an organic solvent, which is preferably composed of dichloromethane. In principle a series of organic liquids like aromatic solvents (like benzene), ethers (like dioxane) and other aprotic solvents (like dimethylformamide) are suitable solvents in which the aminolysis of the invented method can be executed. However, the solvent dichloromethane has the additional advantage that it is particularly inert towards the reaction conditions used, while dissolving the reactants in a sufficient degree. In view of safety regulations, toluene is considered to be a very attractive candidate to replace the other suitable solvents mentioned in this paragraph. It is observed that the reaction can in principle be performed under neat (i.e. solvent-free) conditions. Initial experiments showed however a lower conversion under such neat conditions.

Another interesting embodiment of the claimed invention is characterized in that N,N-dialkyllactamide formed in the reaction mixture is distilled, preferably after extraction. These steps provide result in a simple method for purifying the product obtained with the invented method. Dichloromethane on the one hand side and N,N-dialkyllactamide or N,N-dialkyllactamide on the other hand can simply be separated by means of distillation. This holds especially for the more simple N,N-dialkyllactamides, like N,N-dimethyllactamide, N,N-methylethyllactamide and N,N-diethyllactamide. The extraction step can be performed by adding an amount of an aqueous solution to the reaction mixture. Such aqueous solution is preferably an alkaline aqueous solution. In this step two immiscible layers are formed, an aqueous layer and an organic layer. The final product can be obtained in pure form by distilling it from the organic layer.

A still another interesting embodiment of the invention has the feature that formed N,N-dialkyllactamide is subsequently halogenated by means of $SOX_2$, whereby X stands for a halogen atom, preferably for chloride. In this reaction, the hydroxy group of the N,N-dialkyllactamide is exchanged for a halogen group, preferably a chloride group. This reaction can be performed with relatively great ease when the lactamide compound is N,N-dimethyllactamide, N,N-methylethyllactamide or—preferably—N,N-diethyllactamide. This halogenation reaction is done preferably under neat (solvent-free) conditions at slightly elevated temperatures (40-70° C.) and with the aid of a catalyst. Compounds suitable as catalyst for this reaction have been published previously in the scientific publication Green Chem., 2014, 16, 3993-3998.

According to a preferred embodiment of the present invention, the formed halogenated N,N-diethyllactamide is subsequently reacted with α-hydroxy naphthalene in the presence of a base. In this reaction, the compound N,N-diethyl-2-(1-naphthalenyloxy)propanamide is formed. The mentioned reaction is preferably executed in a polar aprotic solvent under slightly elevated temperatures (60-80° C.). The base used in this conversion reaction is preferably $K_2CO_3$.

It is known that the (R)-enantiomer of the compound mentioned in the previous paragraph has a significantly higher herbicidal activity compared to the (S) enantiomer. In view of this, the invented method to produce optically pure N,N-dialkyllactamide is very interesting, as this method allows one to produce (R)—N,N-diethyllactamide with a high optical purity in an efficient manner, which compound can be converted by the method described before in a relatively simple and efficient manner into the interesting (R)—N,N-diethyl-2-(1-naphthalenyloxy)propanamide.
With proper choice of the starting material selected from optically pure alkyl (R) lactate, (R,R)-lactide and (R)-PLA, an optical purity of the compound (R)—N,N-diethyllactamide of at least 99.0%, preferably at least 99.5% and more preferably at least 99.9% can be achieved.

DESCRIPTION OF EMBODIMENTS

The method according to the invention is elucidated by means of the following examples.

Example 1

A three-necked round bottom flask was loaded with anhydrous aluminum chloride (17.35 g) and dichloromethane (30 mL). External cooling was facilitated with ice water, and diethylamine (18 g) was added drop wise over the course of 30 minutes, keeping the internal temperature below 35° C. D-lactide (7.21 g Puralact-D, having optical purity of at least 99.9%) was dissolved in 20 mL dichloromethane and added drop wise to the reaction mixture over the course of 30 minutes during stirring of the mixture. A temperature of below 35° C. was maintained by external cooling with ice, and adjusting the addition speed. After adding all the lactide, the reaction mixture was stirred for an additional 30 minutes, after which the reaction appeared to be complete (as determined by GC analysis).

Subsequently, a sodium hydroxide solution (6M, 50 mL) was added stepwise to the mixture. A two phase system of an organic layer and an aqueous layer was formed. The organic layer was collected and the aqueous layer was washed with dichloromethane. The combined organic layers were evaporated to dryness. The crude product was distilled and yielded (R)—N,N-diethyllactamide (82% yield, >99% pure compound, >99% enantiomeric excess) as a colorless liquid. The optical purity of the obtained (R) N,N-diethyl-lactamide was determined by means of GC using a β-cyclodextrine column, as described before.

Example 2

Aluminum chloride (579 g) was loaded into a 3 necked round bottom flask sufficient for the total volume. Dichloromethane (1 L) was added. The mixture was stirred with a magnetic stirrer. Diethylamine (610 g) was added drop wise, while the mixture was cooled externally using an ice bath. When the addition was complete, methyl-(R)-lactate (347 g, Purasolve ML/D having optical purity >99% enantiomeric excess) was added drop wise to the reaction mixture over the course of 30 minutes during stirring of the mixture. The temperature was kept below 40° C. with the aid of external cooling. After adding all the methyl-(R)-lactate, the reaction mixture was stirred for an additional 30 minutes, after which the reaction appeared to be complete (as determined by GC analysis).

Sodium hydroxide solution (6M, 1.7 L) was added stepwise to the mixture. A two phase system having an organic layer and an aqueous layer was formed. The organic layer was collected and the aqueous top layer was washed with dichloromethane. The combined organic layers were evaporated to dryness. The crude product was distilled and yielded (R)—N,N-diethyllactamide (74% yield, >99% pure product, >99% enantiomeric excess) as a colorless liquid. The optical purity of the obtained (R)-diethyllactamide was determined by means of GC using a β-cyclodextrine column, as described before.

Example 3

Lactic acid (174 g) was added in a 3-necked 250 ml round bottom flask. Heating was started at atmospheric pressure to reach 150° C. At that temperature the first drops of condensate were observed. The temperature was further increased to 180° C. and the pressure was reduced stepwise to 50 mbar. After 4 h, an acid value (AV) was measured of 110 mg KOH/g and the reaction was stopped. The so-formed PLA oligomer product (with n of approximately 10) was poured on a metal plate to cool down and subsequently crushed to make it easier to handle for the next step.

Aluminum chloride (17 g) and dichloromethane (30 mL) were added in a 250 ml 3-necked round bottom flask and stirred via magnetic stirring plate. After slow addition of diethylamine, the PLA oligomer product was added in portions. The reaction was stirred overnight at room temperature.

Subsequently, sodium hydroxide solution (6M, 100 mL) was added stepwise to the mixture. A two phase system having an organic layer and an aqueous layer was formed. The organic layer was collected and the aqueous top layer was washed with dichloromethane. The combined organic layers were evaporated to dryness. The crude product was distilled and yielded (R)—N,N-diethyllactamide (59% yield, 99+% pure compound, >91% enantiomeric excess) as a colorless liquid. The optical purity of the obtained (R)—N,N-diethyllactamide was determined by means of GC using a β-cyclodextrine column, as described before.

Example 4

(R)—N,N-Diethyllactamide (10 g; 69 mmol, optical purity >99 enantiomeric excess) was put in a round bottomed flask together with dichloromethane (50 mg, 0.7 mmol, 0.01 eq.) and a drop of dimethylformamide under inert conditions. The thus formed reaction mixture was heated to 65° C. Thionyl chloride (9 g, 76 mmol) was added drop wise, during which gas was expelled from the reaction mixture and the temperature rose to 87° C. After stirring for 4 h, no (R)—N,N-diethyllactamide could be detected by means of GC, and the reaction was therefore considered complete.

The reaction mixture was allowed to cool to room temperature, and water (20 mL) was added drop wise. The temperature rose to 40° C. during the water addition. Brine (20 mL) was added and the formed organic and aqueous layers were separated. The crude product was isolated as a colorless liquid from the organic layer. The crude product was distilled and the final product was obtained as a colorless, oil-like liquid (10 g). The oil-like liquid was dissolved in dimethylformamide (100 ml), and $K_2CO_3$ (12 g) and naphthol (10 g) were added to this solution. The thus formed reaction mixture was stirred for 6 h at 60° C. After this period, the reaction was neutralized with HCl (aqueous). Toluene was added and the layers were separated. The organic phase was evaporated to dryness and the crude product was recrystallized in ethanol, yielding (R)—N,N-diethyl-2-(1-naphthalenyloxy)-propanamide as a solid (11 g).

The invention claimed is:

1. A method for the manufacture of N,N-dialkyllactamide having an optical purity of at least 99.0%, whereby at least one of the compounds selected from the series consisting of alkyl lactate, lactide and polylactic acid is mixed with dialkylamine in order to form a reaction mixture, under conditions whereby aminolysis takes place in the reaction mixture, wherein in the method:
   substantially no racemization occurs;
   alkyl stands for at least one of methyl or ethyl; and
   the reaction mixture further comprises a Lewis acid selected from the group consisting of aluminum chloride ($AlCl_3$), aluminum bromide ($AlBr_3$) and anhydrous ferric chloride ($FeCl_3$).

2. The method according to claim 1, wherein $AlCl_3$ is used as a Lewis acid.

3. The method according to claim 1, wherein the at least one compound selected from the series consisting of alkyl lactate, lactide and polylactic acid is optically pure.

4. The method according to claim 1, wherein the amount of the Lewis acid in the reaction mixture is in the range of 0.3-1.2 mole equivalents, based on the amount of lactic acid units of the compounds in the reaction mixture.

5. The method according to claim 1, wherein the reaction mixture comprises an organic solvent.

6. The method according to claim 1, wherein N,N-dialkyllactamide formed in the reaction mixture is distilled.

7. The method according to claim 1, wherein formed N,N-dialkyllactamide is subsequently halogenated by means of $SOX_2$, whereby X stands for a halogen atom.

8. The method according to claim 7, wherein the formed halogenated N,N-dialkyllactamide is subsequently reacted with α-hydroxy naphthalene in the presence of a base.

9. The method according to claim 8, wherein the base is $K_2CO_3$.

10. The method according to claim 5, wherein the organic solvent is composed of dichloromethane.

11. The method according to claim 6, wherein N,N-dialkyllactamide formed in the reaction mixture is distilled after extraction.

12. The method according to claim 6, wherein formed N,N-dialkyllactamide is subsequently halogenated by means of $SOX_2$, wherein X is a halogen atom.

13. The method according to claim 7, wherein X is chloride.

14. The method according to claim 12, wherein the formed halogenated N,N-dialkyllactamide is subsequently reacted with α-hydroxy naphthalene in the presence of a base.

15. A method for the manufacture of N,N-dialkyllactamide, whereby at least one of the compounds selected from the series consisting of alkyl lactate, lactide and polylactic acid is mixed with dialkylamine in order to form a reaction mixture, under conditions whereby aminolysis takes place in the reaction mixture, wherein in the method:
the reaction mixture further comprises a Lewis acid selected from the group consisting of aluminum chloride ($AlCl_3$), aluminum bromide ($AlBr_3$) and anhydrous ferric chloride ($FeCl_3$); and
the N,N-dialkyllactamide formed in the reaction mixture is distilled after extraction.

16. The method according to claim 15, wherein the N,N-dialkyllactamide formed in the reaction mixture is extracted by adding an aqueous alkaline solution to said reaction mixture.

17. A method for the manufacture of N,N-dialkyllactamide, whereby at least one of the compounds selected from the series consisting of alkyl lactate, lactide and polylactic acid is mixed with dialkylamine in order to form a reaction mixture, under conditions whereby aminolysis takes place in the reaction mixture, wherein in the method the reaction mixture further comprises:
a Lewis acid selected from the group consisting of aluminum chloride ($AlCl_3$), aluminum bromide ($AlBr_3$) and anhydrous ferric chloride ($FeCl_3$); and
an organic solvent comprised of dichloromethane.

* * * * *